US008425406B2

(12) United States Patent
Smith et al.

(10) Patent No.: US 8,425,406 B2
(45) Date of Patent: Apr. 23, 2013

(54) SYSTEMS AND METHODS FOR DIRECTING INSTRUMENTS TO VARYING POSITIONS AT THE DISTAL END OF A GUIDE TUBE

(75) Inventors: Paul J. Smith, Smithfield, RI (US);
Katie Krueger, Merrimack, NH (US);
Barry Weitzner, Acton, MA (US);
Andy Campbell, Reading, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 571 days.

(21) Appl. No.: 12/640,424

(22) Filed: Dec. 17, 2009

(65) Prior Publication Data

US 2010/0160729 A1 Jun. 24, 2010

Related U.S. Application Data

(60) Provisional application No. 61/139,033, filed on Dec. 19, 2008.

(51) Int. Cl.
*A61B 1/00* (2006.01)

(52) U.S. Cl.
USPC .......................................... 600/114; 600/153

(58) Field of Classification Search .................. 600/114, 600/153
See application file for complete search history.

(56) References Cited

U.S. PATENT DOCUMENTS

| 4,706,656 | A | 11/1987 | Kuboto |
| 4,784,117 | A | 11/1988 | Miyazaki |
| 4,971,035 | A | 11/1990 | Ito |
| 5,503,616 | A | 4/1996 | Jones |
| 6,152,871 | A | 11/2000 | Foley et al. |
| 7,775,968 | B2 * | 8/2010 | Mathis .......................... 600/114 |
| 7,815,565 | B2 * | 10/2010 | Stefanchik et al. ........... 600/114 |
| 2007/0167680 | A1 | 7/2007 | Miyamoto et al. |
| 2011/0124960 | A1 * | 5/2011 | St. Onge et al. .............. 600/104 |

FOREIGN PATENT DOCUMENTS

| EP | 1 284 120 A1 | 2/2003 |
| EP | 1 426 005 A1 | 6/2004 |

OTHER PUBLICATIONS

International Search Report and Written Opinion issued in PCT/US2009/068767; Date of mailing: Apr. 20, 2010.
Patil et al. "Effect of the angle between the optical axis of the endoscope and the instruments' plane on monitor image and surgical performance," *Surgical Endoscopy* 18(1):111-114 (2004), abstract.

* cited by examiner

*Primary Examiner* — Christopher Mahoney
(74) *Attorney, Agent, or Firm* — Bookoff McAndrews, PLLC

(57) ABSTRACT

Described herein are various systems and methods for directing endoscopy instruments to varying positions at a target site. In one aspect, at least one instrument channel has multiple exit points at the distal end of the guide tube, and the position of an instrument delivered through the channel may be switched between the different exit points. In another aspect, an instrument channel splits into multiple branches at the distal end of the guide tube, and the position of an instrument at the target site may be changed by selectively directing the instrument into a different channel branch. In yet another aspect, the guide tube, or a portion thereof, may be rotated to reposition an instrument at the target site. The capability of changing the instrument positions during a procedure would enable a physician to examine or treat multiple target sites within an operative field, without necessitating the full retraction of the instruments or the guide tube from the operative field.

35 Claims, 3 Drawing Sheets

SYSTEMS AND METHODS FOR DIRECTING INSTRUMENTS TO VARYING POSITIONS AT THE DISTAL END OF A GUIDE TUBE

The present disclosure claims priority to U.S. Provisional Application No. 61/139,033, filed on Dec. 19, 2008, which is incorporated herein by reference in its entirety.

BACKGROUND OF THE INVENTION

Endoscopic surgery, also known as minimally invasive surgery, uses an endoscope delivered through a small body incision or a natural body orifice to collect images of the surgical site. Conventional endoscopes usually include two fiber optic lines for image collection—a "light fiber" which carries light into the body cavity, and an "image fiber" which carries the image of the body cavity back to the physician's viewing lens. Such endoscopes can further include a separate axial port or working channel for administration of drugs, suction, and irrigation. This working channel may also be used to introduce small surgical instruments or end-effectors, such as forceps, scissors, brushes, etc. for tissue excision, sampling, or other diagnostic and surgical work. The goal of endoscopic surgery is to reduce tissue trauma and the body's response to the injury of traditional (or open) surgery. Examples of endoscopic surgery include laparoscopic cholecystectomies (gall bladder removal) and appendectomies; arthroscopic surgery of the interior of bone joints; endoscopic rhinosinusitis; colonoscopic excisions, endoscopic discectomy, etc. In addition, endoscopic tools may be used for visualization and manipulation of architectural scale models, complex technical systems, improvised explosive devices, and other non-medical applications.

The growing capabilities of endoscopic tools have allowed physicians to perform an increasing variety of surgeries and diagnostic procedures through small body openings. Further refinement of the endoscopic devices may enable the physicians to access the target sites through even less invasive routes, and thereby cause less post-operative pain, less scar tissue formation, and shorten the recovery time. Improvement in the design and functionality of the minimally invasive tools would make endoscopic procedures feasible for body regions not accessible with conventional endoscopic tools, and would contribute significantly towards the advancement of translumenal endoscopic surgeries via natural orifices.

SUMMARY OF THE INVENTION

Described herein are systems and methods for directing instruments to varying positions at a target site relative to anatomic structure, other instruments, and/or a guide tube. In one aspect, the system comprises an elongate guide tube extending between a proximal end and a distal end, and includes two or more channels for the delivery of instruments to the target site. The channels in the guide tube comprise a point of entry at the proximal end of the guide tube, and a point of exit at the distal end of the guide tube. At least one of the channels further comprises an additional exit point at the distal end. An instrument positioned in one of the exit points may be switched to a different exit point in order to direct the instrument to a different position relative to another instrument, the guide tube, and/or the target site.

In another aspect, the system comprises an elongate guide tube extending between a proximal end and a distal end, wherein the guide tube includes multiple exit points for instruments at the distal end, and at least two of the exit points are connected by a common lumen. The common lumen is configured to receive an instrument at the proximal end of the guide tube, and the instrument may be selectively positioned at any of the distal exit points connected to the lumen.

In yet another aspect, the system comprises an elongate guide tube extending between a proximal end and a distal end, and having two or more working channels to deliver instruments to a target site. The guide tube is rotatable about a longitudinal axis, such that an instrument delivered to the target site can be rotated to a different position by rotating the guide tube.

In one embodiment, only a portion of the guide tube rotates around a longitudinal axis of the guide axis. In another embodiment, the guide can be segmented and only a segment of the guide tube is rotatable around the longitudinal axis.

Further described herein are methods for directing instruments to varying positions at the distal end of a guide tube. In one embodiment, the guide tube comprises multiple exit points for instruments at its distal end, and the exits are interconnected via a passage. An instrument positioned in one of the exit points may be redirected to another exit point through the interconnecting passage to enable the instrument to access a different target location.

In another embodiment, the guide tube comprises multiple exit points for instruments at its distal end, and at least two of the exit points are connected by a common lumen. An instrument may be introduced into the guide tube through the common lumen, and positioned at any of the exit points connected to the lumen. To repositioning the instrument at the target site, the instrument may be withdrawn into the common lumen, and redirected to another exit point connected to the lumen.

In yet another embodiment, the entire guide tube, or a section thereof, is rotatable around a longitudinal axis. An instrument may be delivered to a target site through a channel in the guide tube. To reposition the instrument at the target site, the entire guide tube, or a rotatable section thereof, may be rotated to redirect the instrument to a different position relative to the target site.

The applications of the disclosed systems and methods include, but are not limited to, trans-oral, trans-anal, trans-vaginal, trans-nasal, laparoscopic, arthroscopic, thoracoscopic, panendoscopic surgeries, etc. In addition, the disclosed systems and methods may be used for various diagnostic applications, such as collection of tissue biopsy samples, gastroscopy for visualization of ulcers within the upper GI tract, hysteroscopy for diagnosis of intrauterine pathology, etc. The systems and methods disclosed herein may also be used for non-medical applications, such as in the inspection and/or repair of machinery.

It is to be understood that both the foregoing general description and the following detailed description are exemplary and are not restrictive of the invention, as claimed.

DETAILED DESCRIPTION OF THE INVENTION

Figure 1A:
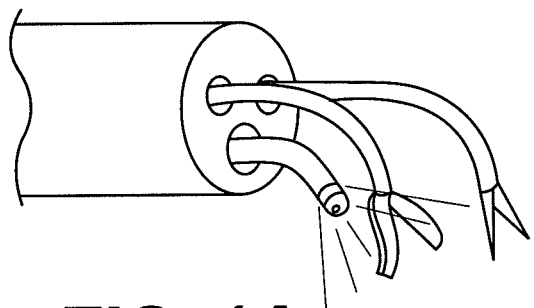
FIG. 1A shows a perspective view of the distal end of a guide tube, depicting an optical device and two surgical instruments exiting the guide tube at a target site.
Figure 1B:
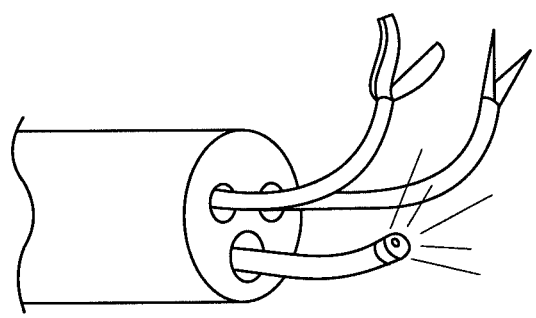
FIG. 1B illustrates the distal end of a guide tube, wherein the optical device and the surgical instruments, as referred to in FIG. 1A, are rotated to access a different target site.
Figure 1C:
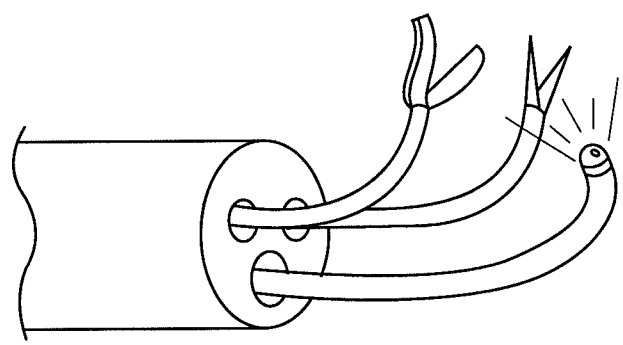
FIG. 1C illustrates the distal end of a guide tube, wherein the optical device, as referred to in FIG. 1A, is articulated to acquire an unobscured view of a target site.

Disclosed herein are systems and methods for directing instruments to varying positions at a target site for performing various endoscopic procedures. As depicted in FIG. 1A, therapeutic and diagnostic endoscopy facilitate the triangulation of an optical device and surgical instruments (such as, forceps, scissors, tissue graspers, etc.) within a guide tube in order to obtain a clearer view of the operative field, while allowing a wide range of motion of the instruments. Triangulating endoscopes permit concomitant retraction and dissection of tissue. For certain translumenal endoscopic procedures, it may be desirable to change the position and/or orientation of the optics and the surgical instruments when moving from a first target area to a second target area. However, changing the orientation of the surgical instruments, without changing the relative position of the optics, as depicted in FIG. 1B, may obscure the view of the target site. In the prior art, articulation of the optical device with respect to the other instrument positions has been shown to provide better visual clarity, as illustrated in FIG. 1C. However, large articulation of the optics would alter the viewing angle of the operative field, which is often undesirable during an endoscopic procedure.

Disclosed herein are various systems and methods for changing the relative position of the optics, and/or the surgical instruments without necessitating the retraction of the guide tube from the target site. The present disclosure may generally refer to both optical devices and surgical instruments as "instruments" for convenience hereinafter. The described systems and methods may be applied to any optical and surgical/diagnostics instruments used with an endoscopic system.

Figure 2:
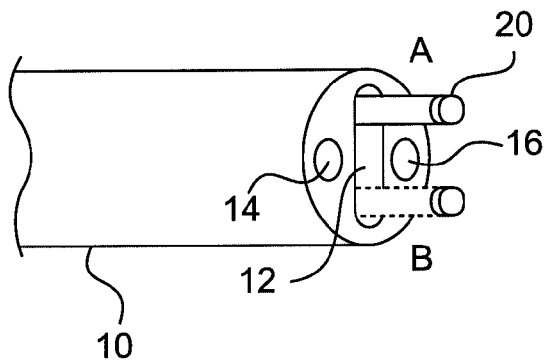
FIG. 2 shows a perspective view of the distal end of a guide tube, having an instrument channel with multiple exit points.

In one aspect, an endoscopic guide tube may include an instrument channel having multiple exit points, and the position of an instrument at the target site may be switched by redirecting the instrument to a different exit point of the channel. FIG. 2 illustrates a perspective view of the distal end of an endoscopic guide tube 10 used for performing surgeries or diagnostic tests through a natural orifice or a small surgical incision. Guide tube 10 includes multiple channels 12, 14 and 16 for delivery of instruments to the target site during an endoscopic procedure. The size and shape of channel 12 provides multiple exit positions to an instrument 20 delivered through the channel. The exit positions of the instrument may be alternated by moving instrument 20 within channel 12. More specifically, the position of instrument 20, delivered through channel 12, may be changed from a first position "A" to a second position "B" during the procedure without affecting the position of any instrument in channels 14 and 16. The position of the instrument may be switched by using a tool for directional steering or lateral displacement of an object in a lumen, such as internal balloon, cam, guide wire, etc. The directional steering device within the channel can also hold the instrument in a first or second position, and inhibit unwanted movement of the instrument relative to the other instruments and/or the guide tube during a procedure.

Figure 3A:
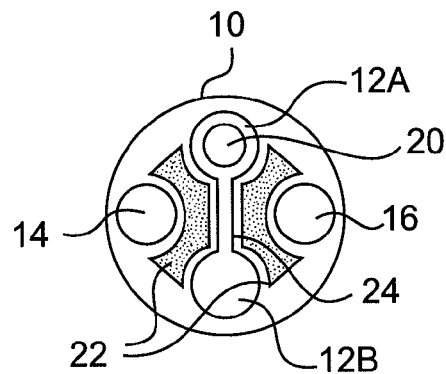
FIG. 3A illustrates a cross-section of the distal end of a guide tube, wherein multiple exit points are interconnected by a narrow passage and the area surrounding the passage is void to allow expansion of the passage.
Figure 3B:
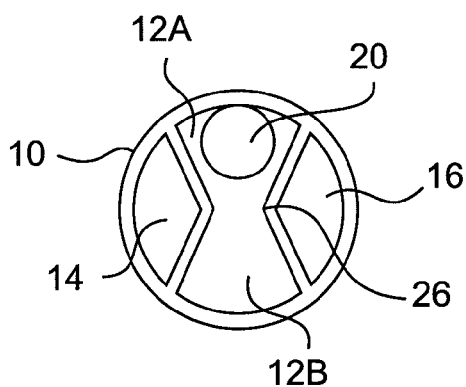
FIG. 3B illustrates a cross-section of the distal end of a guide tube, wherein an instrument channel with multiple exit points is constricted in the central region to prevent inadvertent displacement of an instrument placed in one of the exits.

In another aspect, the instrument channel is configured to inhibit movement of the instrument within the channel. An instrument placed in one of the exit positions can be locked in position relative to the guide tube by the wall of the channel. The multiple exit points of the channel may be defined by a narrow central region of the channel, as shown in FIG. 3A and FIG. 3B. The multiple exit points in the channel are interconnected by a traversable passage. The width of the passage is smaller than the cross-sectional diameter of an instrument delivered through the channel, which inhibits unwanted movement of the instrument from a first exit point to a second exit point through the narrow central region. An instrument placed in one of the exit points may be shifted to a different exit point through the interconnecting passage by means of some lateral force applied to the instrument by an user. In one embodiment, the channel is constricted only at the distal end of the guide tube, such that the multiple exit points are defined only near the distal end of the channel. In another embodiment, the constricted region extends throughout the length of the channel, defining two individual lumens within the channel connected by a traversable passage.

FIG. 3A illustrates a cross-section of the distal end of guide tube 10. Channel 12 in the guide tube includes two exit points 12A and 12B, which are interconnected by a passage 24. Passage 24, and the area of the guide tube surrounding the passage, are configured such that passage 24 can expand to allow the transfer of instruments from one exit point to another. In one embodiment, as illustrated in FIG. 3A, area 22 surrounding the channel is void, so that passage 24 can expand radially to allow the transfer of instrument 20 from exit 12A to 12B. The presence of the void region allows passage 24 to expand without impinging on the other instrument channels in the guide tube, such as channels 14 and 16.

In another embodiment, illustrated in FIG. 3B, channel 12 similarly includes a narrow central region 26 to inhibit unwanted movement of an instrument between a first and a second position. The area of the guide tube surrounding central region 26 is flexible, deformable, elastic, or compressible, so that the channel can expand to allow the passage of instrument 20 from exit 12A to 12B. As described earlier, the narrow region can be at the distal end of the channel 12, or throughout the length of channel 12. In one embodiment, an additional instrument may be delivered through narrow central region 26, which would prevent inadvertent passage of instrument 20 to other exit points. In another embodiment, positioning instruments in channels 14 and 16 can inhibit channel 12 from expanding, and thereby, locks instrument 20 in a first or a second exit position.

In yet another embodiment, the placement of an instrument in a first or a second position causes deformation of the channel and prevents movement of the instrument to a different position. In such an embodiment, at least a portion of the walls of channel 12 can be defined by a flexible member. Insertion of an instrument into a first or a second exit position changes the shape of channel 12. In particular, instrument 20 can have a larger cross-section than channel 12. Inserting the instrument into channel 12 deforms the walls of channel 12 and changes the shape of the channel. In one embodiment, the unused exit position is reduced in area by the insertion of instrument 20. In addition, insertion of instrument 20 can change the shape of channels 14 and 16.

Figure 3C:
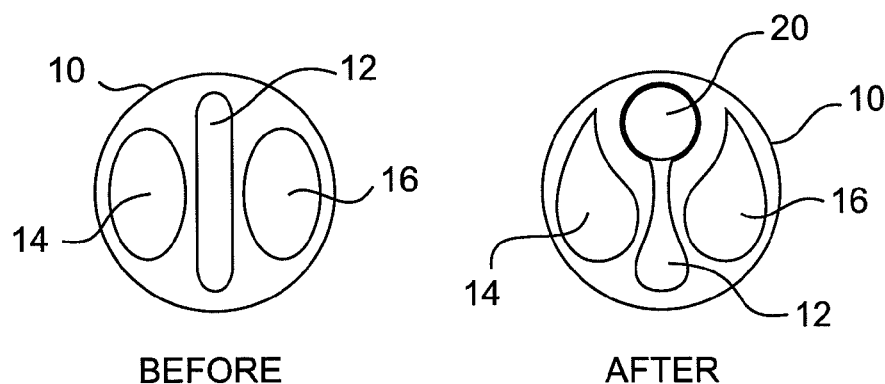
FIG. 3C illustrates a cross-section of the distal end of a guide tube having an instrument channel with multiple exit points (BEFORE), wherein the exit points expand radially when occupied by an instrument (AFTER).

In one embodiment, the removal of instrument 20 from an exit position causes channel 12 to return to its original shape, and consequently, the other channels in the guide tube regain their original configuration. As illustrated in FIG. 3C, insertion of instrument 20 into exit 12A causes it to expand, which deforms the profile of exits 12B, and channels 14 and 16 of guide tube 10. The change in the shape of exit 12B would prevent any involuntary displacement of instrument 20 from exit 12A to 12B during a procedure. Exit 12A contracts into its original shape and size when instrument 20 is removed from it, and accordingly, exit 12B and channels 14 and 16 regain their original configurations. Instrument 20 may then be positioned in exit 12B if required by the procedure.

In another embodiment, the removal of instrument 20 from a first exit position does not automatically restore the shape of channel 12. The subsequent insertion of instrument 20 into a second exit position of channel 12 may restore the shape of the channel, or deform it further.

Figure 4:
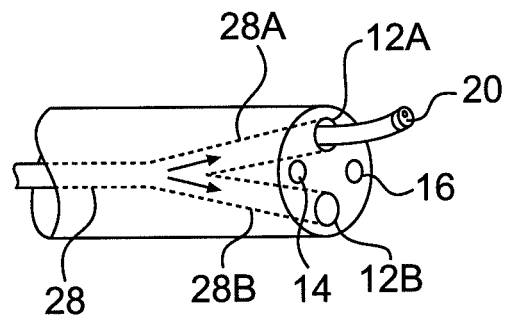
FIG. 4 shows a perspective view of the distal end of a guide tube, having an instrument channel that splits into multiple branches at the distal end, such that an instrument delivered through the channel may exit the guide tube via any of the channel branches.

In another aspect, the distal end of a guide tube includes multiple exit points for instruments introduced into the guide tube. At least two of the exit points are connected by a common lumen, such that an instrument introduced into the guide tube through the common lumen may be positioned at any of the distal exit points connected to the lumen. FIG. 4 illustrates an embodiment where the distal end of guide tube 10 includes multiple instrument exit points 12A, 12B, 14 and 16. Exit points 12A and 12B are connected by a common lumen 28. That is, common lumen 28 bifurcates into two branches 28A and 28B, which are connected to exit points 12A and 12B. Common lumen 28 is configured to receive instrument 20 at its proximal end, and the instrument may be positioned at either exit 12A or 12B depending on the procedural requirements. If the position of the instrument has to be changed during the procedure, the instrument may be retracted from the exit point into the common lumen, and then redirected into the other exit connected to the lumen. This method of alternating the position of the instrument saves the physician valuable time during an endoscopic procedure, since the instrument does not have to be retracted all the way out of the guide tube for reinsertion into a different exit point.

Figure 5:
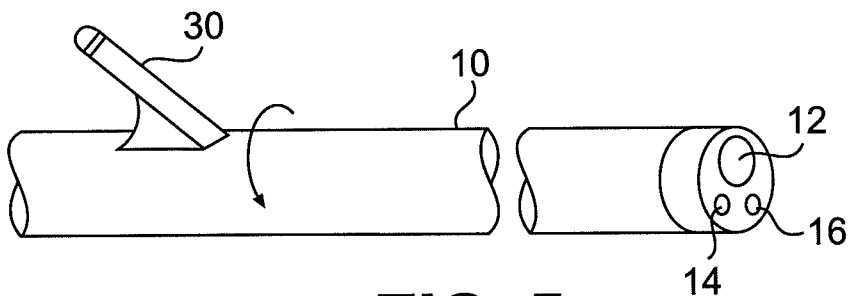
FIG. 5 shows a perspective view of a guide tube that may be rotated to change the position of an instrument at the target site.

In yet another aspect, the guide tube may be rotated around a longitudinal axis to reposition the instrument at the target site. FIG. 5 illustrates a perspective view of guide tube 10 having three working channels for the delivery of instruments to a target site. Instruments may be entered into the channels either from the proximal most end of the guide tube, or through a proximal opening 30. The configuration of the distal exit points, 12, 14 and 16, facilitate triangulation of the instruments delivered into guide tube 10. Guide tube 10 may be rotated to alter the position of an instrument from one quadrant of the operative field to another, while still maintaining the triangulated configuration. If the instruments and/ or the guide tube are mounted on a frame, they may be detached from the frame prior to rotating the guide tube, and reconnected to the frame after the instrument positions at the target site are reconfigured. Alternatively, the guide tube and/ or the instruments can be rotatably connected to the frame. In another embodiment, the frame, or a portion thereof, can rotate with the guide tube and/or the instruments.

Figure 6A:
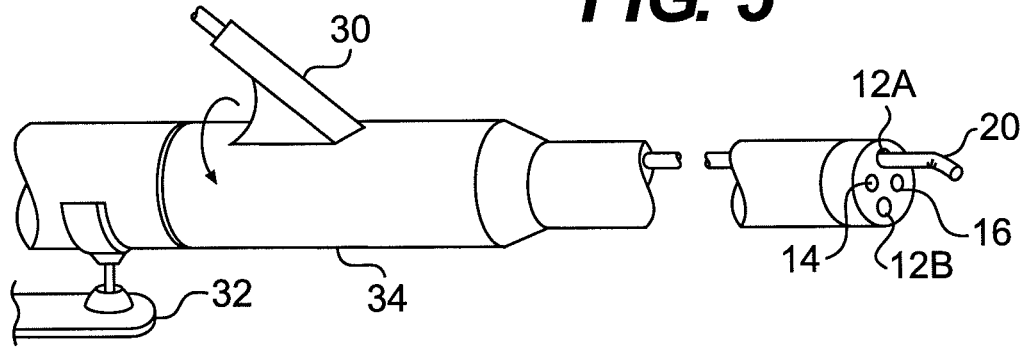
FIG. 6A shows a perspective view of a guide tube, wherein only a portion of the tube may be rotated to change the position of an instrument at the target site.
Figure 6B:
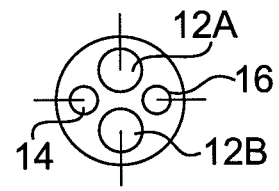
FIG. 6B illustrates a cross-section of the distal end of a guide tube, wherein the instrument exit points are distributed symmetrically around a central longitudinal axis of the guide tube.

In another aspect, only a portion of the guide tube is rotatable about a central longitudinal axis. As illustrated in FIG. 6A, guide tube 10 has multiple instrument exit points at the distal end, which are connected to working channels traversing through the guide tube. Multiple exit points 12A, 12B, 14 and 16, are distributed symmetrically around the central rotation axis, as further elucidated in FIG. 6B. Guide tube 10 is connected to a frame 32, but a portion 34 of the guide tube, which is not directly connected to frame 32, is rotatable about a central longitudinal axis of the tube. Portion 34 of the guide tube also includes proximal opening 30 through which instruments may be introduced or retracted into the working channels. If the position of instrument 20 at the target site needs to be changed, the instrument may be retracted into rotatable portion 34 using proximal opening 30. Portion 34 may then be rotated 180° about the central axis, and instrument 20 may be reinserted into the symmetrically opposite exit 12B. Such an arrangement allows an user to maintain the triangulated positioning of the optics and the instruments in the operative field.

Figure 7:
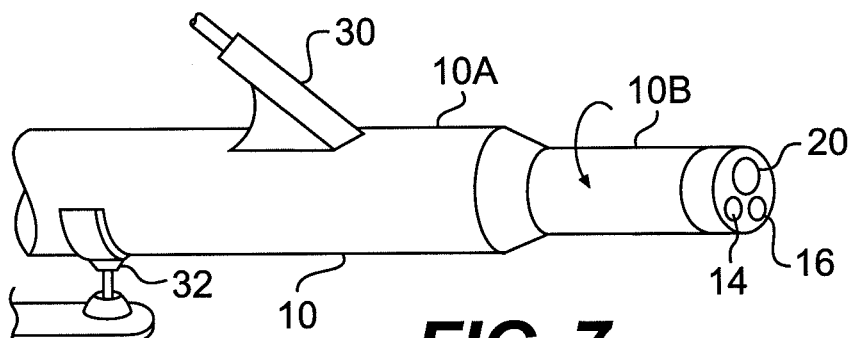
FIG. 7 shows a perspective view of a segmented guide tube, wherein the distal segment may be rotated to change the position of an instrument at the target site.

In yet another embodiment, a distal segment of the guide tube may be rotated to reposition the instruments at the target site. As illustrated in FIG. 7, guide tube 10 is divided into segments 10A and 10B, where distal segment 10B is rotatable via a guide wire or other control means introduced through a hollow channel that passes along a longitudinal axis of proximal segment 10A. Distal segment 10B includes multiple instrument exit points 12, 14 and 16, configured such that they facilitate triangulation of the instruments at the target site. To change the position of the instruments at the target site, the instruments may be retracted into proximal segment 10A, distal segment 10B may then be rotated either clockwise or anticlockwise to change the angular positions of exit points 12, 14 and 16, and the instruments may then be redirected into the exits points. Thus, the position of the instruments would be changed from one quadrant of the operative field to another.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A system for delivering instruments to a target site, the system comprising:
   an elongate guide tube extending between a proximal end and a distal end and including two or more channels for the passage of the instruments, wherein at least one of the channels comprises:
      an elongate distal opening defining a first and a second instrument position; and
   a lateral displacement element for moving an instrument delivered through the channel from the first instrument position to the second instrument position.

2. The system of claim 1, wherein the lateral displacement element locks the instrument delivered through the channel in the first or the second instrument position.

3. A system for delivering instruments to a target site, the system comprising:

an elongate guide tube extending between a proximal end and a distal end and including two or more channels for the passage of the instruments, wherein at least one of the channels comprises:

an elongate distal opening defining a first and a second instrument positions; and a narrow passage between the first and the second instrument positions;

wherein the first and second instrument positions are arranged such that when a first instrument delivered through the channel is positioned within the first instrument position, the second instrument position is unoccupied; and wherein the first instrument position is unoccupied after the first instrument delivered through the channel is moved from the first instrument position to the second instrument position.

4. The system of claim 3, wherein the passage is at the distal end of the channel.

5. The system of claim 3, wherein the passage extends between the proximal and distal ends of the channel.

6. The system of claim 3, wherein the width of the passage is smaller than the cross-sectional diameter of the first instrument delivered through the channel.

7. The system of claim 6, wherein the passage locks the first instrument delivered through the channel in the first or the second instrument position.

8. The system of claim 3, wherein the sidewalls of the passage are flexible, deformable, elastic and/or compressible.

9. The system of the claim 3, wherein the area of the guide tube surrounding the passage is flexible, deformable, elastic and/or compressible.

10. The system of the claim 3, wherein the area of the guide tube surrounding the passage is void.

11. The system of claim 3, wherein the elongate guide tube includes an additional channel.

12. The system of claim 11, wherein a second instrument delivered through the additional channel prevents the passage of the first instrument delivered through the channel from the first instrument position to the second instrument position.

13. The system of claim 3, wherein the two or more channels includes a second and a third channel positioned on either side of the elongate distal opening; and wherein the first instrument delivered through the channel passes between the second and the third channels when moved from the first instrument position to the second instrument position.

14. A system for delivering instruments to a target site, the system comprising:

an elongate guide tube extending between a proximal end and a distal end and including two or more channels for the passage of the instruments, wherein at least one of the channels comprises:

an elongate distal opening defining a first instrument position and a second instrument position; and deformable sidewalls at the distal opening of the channel;

wherein the first and second instrument positions are arranged such that when a first instrument delivered through the channel is positioned within the first instrument position the second instrument position is unoccupied; and wherein the first instrument position is unoccupied after the first instrument delivered through the channel is moved from the first instrument position to the second instrument position.

15. The system of claim 14, wherein insertion of the first instrument into the first or the second instrument position causes deformation of the sidewalls and changes the shape of the channel.

16. The system of claim 15, wherein insertion of the first instrument into the first instrument position reduces the cross-sectional area of the second instrument position.

17. The system of claim 15, wherein insertion of the first instrument into the first or the second instrument position changes the shape of the other channels in the guide tube.

18. The system of claim 17, wherein removal of the first instrument from the first or the second instrument position restores the shape of the channels in the guide tube.

19. A system for delivering instruments to a target site, the system comprising:

an elongate guide tube extending between a proximal end and a distal end and comprising multiple instrument exit points at the distal end, wherein at least two of the exit points are connected by a common lumen bifurcated into two passages.

20. The system of claim 19, wherein an instrument delivered through the common lumen can be inserted into any of the multiple instrument exit points connected to it.

21. A system for delivering instruments to a target site, the system comprising:

an elongate guide tube extending between a proximal end and a distal end and comprising multiple instrument exit openings at the distal end including a first exit opening and a second exit opening, wherein the guide tube is rotatable about a longitudinal axis of the guide tube to move a first instrument from the first exit opening to the second exit opening.

22. The system of claim 21, wherein only a portion of the guide tube rotates around the longitudinal axis.

23. The system of claim 21, wherein the guide tube is segmented and only one of the segments is rotatable around the longitudinal axis.

24. A method for delivering instruments to a target site with an elongate guide tube extending between a proximal end and a distal end and including two or more channels for the passage of the instruments, wherein at least one of the channels comprises an elongate distal opening defining a first and a second instrument position and lateral displacement element, the method comprising the steps of:

delivering an instrument to the first instrument position at the distal end of the guide tube; and moving the instrument from the first instrument position to the second instrument position using the lateral displacement element.

25. A method for delivering instruments to a target site with an elongate guide tube extending between a proximal end and a distal end and including two or more channels for the passage of the instruments, wherein at least one of the channels comprises an elongate distal opening defining a first and a second instrument positions and a narrow passage between the first and the second instrument positions, the method comprising the steps of:

delivering an instrument to the first instrument position at the distal end of the guide tube; and applying a lateral force to the instrument by an user to move the instrument from the first instrument position to the second instrument position through the narrow passage.

26. The method of claim 25, wherein the application of the lateral force to the instrument causes the narrow passage to expand.

27. The method of claim 25, further comprising the step of providing a second and a third channel positioned on either side of the elongate distal opening; and
  wherein movement of the instrument from the first instrument position to the second instrument position passes between the second and the third channels.

28. A method for delivering instruments to a target site with an elongate guide tube extending between a proximal end and a distal end and including multiple exit points for the instruments at the distal end, wherein at least two of the exit are connected by a common lumen bifurcated into two passages, the method comprising the steps of:
  delivering an instrument though the common lumen;
  positioning the instrument at a first exit point;
  withdrawing the instrument into the common lumen; and
  redirecting the instrument to a second exit point.

29. A method for delivering instruments to a target site with an elongate guide tube extending between a proximal end and a distal end and having multiple instrument exit openings at the distal end including a first exit opening and a second exit opening, wherein the guide tube is rotatable about a longitudinal axis of the guide tube,
  the method comprising the steps of:
  delivering an instrument to the target site through a first exit opening; and
  rotating the guide tube around the longitudinal axis to shift the position of the instrument at the target site.

30. The method of claim 29, wherein only a portion of the guide tube is rotatable.

31. The method of claim 30, further comprising the steps of retracting the instrument from the first exit opening into the rotatable portion of the guide tube prior to rotation of that portion; and
  reinsertion of the instrument into the second exit opening.

32. The method of claim 31, wherein the first and the second exit openings are positioned symmetrically opposite to each other in the guide tube.

33. The method of claim 30, wherein the guide tube is segmented into a proximal segment and a distal segment and the step of rotating the guide tube comprises rotation of only the distal segment around the longitudinal axis.

34. The method of claim 33, further comprising the steps of retracting the instrument from the second exit opening into the proximal segment prior to rotation of the distal segment; and
  reinsertion of the instrument into the first exit opening such that the second exit opening is unoccupied.

35. The method of claim 33, wherein the proximal segment comprises a control element to rotate the distal segment.

* * * * *

UNITED STATES PATENT AND TRADEMARK OFFICE
CERTIFICATE OF CORRECTION

| | | |
|---|---|---|
| PATENT NO. | : 8,425,406 B2 | |
| APPLICATION NO. | : 12/640424 | |
| DATED | : April 23, 2013 | |
| INVENTOR(S) | : Paul J. Smith et al. | |

It is certified that error appears in the above-identified patent and that said Letters Patent is hereby corrected as shown below:

In the Claims

Claim 14, Col. 7, Line 62, "position" should read --position,--. (the first occurrence)

Claim 28, Col. 9, Line 10, "exit" should read --exit points--.

Signed and Sealed this
Sixth Day of August, 2013

Teresa Stanek Rea
*Acting Director of the United States Patent and Trademark Office*